(12) United States Patent
Dvorak et al.

(10) Patent No.: US 10,731,190 B2
(45) Date of Patent: Aug. 4, 2020

(54) COMPOSITE COMPONENTS FROM ANAEROBIC DIGESTED FIBROUS MATERIALS

(71) Applicants: Stephen W. Dvorak, Chilton, WI (US); John F. Hunt, Mount Horeb, WI (US)

(72) Inventors: Stephen W. Dvorak, Chilton, WI (US); John F. Hunt, Mount Horeb, WI (US)

(73) Assignees: DVO. Inc., Chilton, WI (US); The United States of America as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/856,924

(22) Filed: Apr. 4, 2013

(65) Prior Publication Data

US 2013/0224803 A1 Aug. 29, 2013

Related U.S. Application Data

(63) Continuation of application No. 12/572,871, filed on Oct. 2, 2009, now Pat. No. 8,414,808.

(60) Provisional application No. 61/102,527, filed on Oct. 3, 2008.

(51) Int. Cl.
C12P 19/04 (2006.01)
B09B 3/00 (2006.01)

(52) U.S. Cl.
CPC .............. *C12P 19/04* (2013.01); *B09B 3/00* (2013.01)

(58) Field of Classification Search
CPC .................................................... C12P 19/04

USPC .......................................................... 264/109
See application file for complete search history.

(56) References Cited

U.S. PATENT DOCUMENTS

| | | | |
|---|---|---|---|
| 2,200,107 A | 5/1940 | Weitz |
| 2,202,772 A | 5/1940 | Durdin, Jr. |
| 2,313,434 A | 3/1943 | Grether |
| 2,722,311 A | 11/1955 | Morrison |
| 3,102,364 A | 9/1963 | Pullen |
| 3,372,018 A | 3/1968 | Stocker et al. |
| 3,892,706 A | 7/1975 | Jetzer |
| 3,951,731 A | 4/1976 | Jetzer |
| 3,989,499 A | 11/1976 | Jetzer |

(Continued)

FOREIGN PATENT DOCUMENTS

| | | |
|---|---|---|
| AU | 7637291 | 11/1991 |
| AU | 7637291 B | 11/1991 |

(Continued)

OTHER PUBLICATIONS

Barron, T., "From cow chips to cow barns", Inside Iowa State, May 19, 2000, www.iastate.edu/Inside/2000/0518/cowchips/html.

(Continued)

*Primary Examiner* — Larry W Thrower
(74) *Attorney, Agent, or Firm* — Husch Blackwell LLP

(57) ABSTRACT

The invention relates to composite components and methods of producing composite components. In yet another embodiment, the present invention relates to a method of producing a composite component using anaerobically digested biomass. In still yet another embodiment, the method further comprises using liquid effluent from the digester. In still yet another embodiment, the method further comprises wet-mat forming and cold pressing the anaerobically digested biomass and wet-mat drying under heat and pressure.

20 Claims, 5 Drawing Sheets

(56) References Cited

U.S. PATENT DOCUMENTS

| | | | |
|---|---|---|---|
| 4,111,744 | A | 9/1978 | Reiniger |
| 4,145,007 | A | 3/1979 | Jetzer |
| 4,227,653 | A | 10/1980 | Jetzer |
| 4,623,515 | A | 11/1986 | Frei et al. |
| 4,702,870 | A | 10/1987 | Setterholm et al. |
| 4,753,713 | A | 6/1988 | Gunderson |
| 4,933,125 | A | 6/1990 | Reiniger |
| 4,942,081 | A | 7/1990 | Reiniger |
| 4,994,237 | A | 2/1991 | Login et al. |
| 5,093,051 | A | 3/1992 | Reiniger |
| 5,198,236 | A | 3/1993 | Gunderson et al. |
| 5,277,854 | A | 1/1994 | Hunt |
| 5,366,677 | A | 11/1994 | Mahanov |
| 5,445,329 | A | 8/1995 | Anderson |
| 5,641,449 | A | 6/1997 | Owens |
| 5,655,718 | A | 8/1997 | Anderson |
| 6,190,151 | B1 | 2/2001 | Hunt |
| 6,245,121 | B1 | 6/2001 | Lamy et al. |
| 6,306,997 | B1 | 10/2001 | Kuo et al. |
| 6,451,589 | B1 | 9/2002 | Dvorak |
| 6,518,387 | B2 | 2/2003 | Kuo et al. |
| 6,521,129 | B1 | 2/2003 | Stamper et al. |
| 6,613,562 | B2 | 9/2003 | Dvorak |
| 6,730,223 | B1 | 5/2004 | Anderson et al. |
| 7,078,229 | B2 | 7/2006 | Dvorak |
| 7,179,642 | B2 | 2/2007 | Dvorak |
| 7,594,356 | B2 | 9/2009 | Freund et al. |
| 2004/0041301 | A1 | 3/2004 | Bouldin et al. |
| 2004/0087011 | A1* | 5/2004 | Dvorak ............ 435/290.4 |
| 2005/0274075 | A1 | 12/2005 | Freund et al. |
| 2006/0150495 | A1 | 7/2006 | MacConnell |
| 2007/0256463 | A1 | 11/2007 | Davis |

FOREIGN PATENT DOCUMENTS

| | | | |
|---|---|---|---|
| CN | 1265266 | * | 9/2000 |
| CN | 1265266 | A | 9/2000 |
| JP | 2001251968 | A | 9/2001 |
| WO | 2005100451 | A2 | 10/2005 |

OTHER PUBLICATIONS

Barron, T, "From cow chips to cow barns", Inside Iowa State, May 19, 2000.

Richard, T.L., et al, "thinking ouside the box building materials and other products from animal processed fiber". Agricultural Outlook Forum 2003: Feb. 2003.

Winandy, J, et al , "potential of using anaerobically digested bovine biofiber as a fiber source for wood composites". bioresources.com, 3(4), 1244-1255, (2008).

Matuana, L., "promoting the use of digestate from anaerobic digesters in composite materials", www.msu.edu/~matuana/images/CompositesProjectFinalReport1.pdf; Oct. 24, 2006.

Office Action U.S. Appl. No. 10/867,228 dated Oct. 31, 2008.

Barron, T., "From cow chips to cow barns", Inside Iowa State, May 19, 2000, www.iastate.edu/inside/200/0518/cowchips/html.

"Composite Products may Offer Agriculture Industry New Markets, Construction Industry New Materials", www.plantmanagementnetwork.org/pub/cm/news/2007/CompositeProducts/.

"3D Engineered Fiberboad", Poster shown at the Oct. 2, 2007 World Dairy Expo, Madison WI.

"The History of CowPots", http://www.cowpots.com/history.html, accessed Aug. 28, 2008.

Richard, T.L., et al., "Thinking outside the box: building materials and other products from animal processed fiber", Agricultural Outlook Forum 2003; Feb. 21, 2003.

Winandy, J, et al., "Potential of using anaerobically digested bovine biofiber as a fiber source for wood composites", bioresources.com, 3(4), 1244-1255, (2006).

Spelter, H., et al., "Anaerobically digested bovine biofiber as a source of fiber for particleboard manufacturing; an economic analysis", bioresources.com, 3(4), 1256-1266, (2008).

Tracy, V., "Ecowpots inventor makes haste with bovine waste", http://steve-lewis.blogspot.com/search?q=bovine, Sep. 5, 2008.

www.cowpots.com, 2009.

Mutuana, L., "Promoting the use of digestate from anaerobic digesters in composite materials", www.msu-edu/~matuana/images/CompositesProjectFinalReport1.pdf, Oct. 24, 2006.

Office Action U.S. Appl. No. 10/867,226 dated Oct. 31, 2008.

\* cited by examiner

COMPOSITE COMPONENTS FROM ANAEROBIC DIGESTED FIBROUS MATERIALS

CROSS REFERENCE TO RELATED APPLICATIONS

This application is a continuation patent application of U.S. patent application Ser. No. 12/572,871 filed Oct. 2, 2009, which claims the benefit of U.S. provisional application Ser. No. 61/102,527 filed Oct. 3, 2008. The content of the above-referenced applications are incorporated herein by reference in their entirety.

STATEMENT REGARDING FEDERALLY SPONSORED RESEARCH OR DEVELOPMENT

This invention is jointly owned between Steven Dvorak and USDA and was made with United States government support. The government has certain rights in this invention.

FIELD

The invention relates to composite components and methods of producing composite components from fibrous materials. In yet another embodiment, the invention relates to a method of producing a composite component using anaerobic digested biomass. In still yet another embodiment, anaerobic digested biomass and effluent from the anaerobic digester are used to produce a composite component.

BACKGROUND

Livestock confinement facilities generate large amounts of animal waste that can create serious environmental and human health concerns. For example, animal waste constituents such as organic matter, nitrogen, phosphorus, pathogens and metals can degrade water quality, air quality, and adversely impact human health. Organic matter, for example, contains a high amount of biodegradable organics and when discharged to surface waters will compete for, and deplete the limited amount of dissolved oxygen available, causing fish kills and other undesirable impacts. Similarly nutrient loading from nitrogen and phosphorus can lead to eutrophication of surface waters.

The annual accumulation of organic waste in the world is immense. There are approximately 450,000 Animal Feeding Operations ("AFOs") in the United States. Common types of AFOs include dairies, cattle feedlots, and poultry farms. A single dairy cow produces approximately 120 pounds of wet manure per day. The waste produced per day by one dairy cow is equal to that of 20-40 people. If properly stored and used, manure from animal feeding operations can be a valuable resource.

Anaerobic digesters can be used to process waste fibrous material, such as wood and manure, and convert the material into biogas composed of methane, ammonia, and $CO_2$, and remaining fibrous residuals. The biogas, primarily methane, can be used to produce electricity. The remaining residual fibrous material has been used for cow bedding, land nutrient amendment, or as compost. Large dairies have an abundance of this remaining fibrous material and managers of these dairies would like to have a value-added outlet other than bedding or land application.

Others have experimented with digester solids to determine what type of products could be made from the material; however, to date, methods used to convert fibrous material into other products have been limited. Most experiments have focused on drying the residual material, then combining it with adhesive, and possibly wood, to make an air-laid dry-formed composite board. Others have combined the residual material with plastic to extrude it into various outdoor products. However, these products have been limited in size, shape, strength, utility and industrial applicability.

Therefore, methods that can convert the fibrous residual material into a product of value, such as a composite component, would be extremely useful.

BRIEF SUMMARY

The invention relates to composite components and methods for producing composite components. In one embodiment, the invention relates to a method comprising: digesting waste fibrous material in an anaerobic digester to produce anaerobic digested biomass, and refining the anaerobic digested biomass to produce fibers that are low in carbohydrates and increased in cellulose, and lignin content. Composite components of the invention can be produced in the absence of earthworms, resins, waxes or other added chemical substance often needed to enhance fiber-to-fiber bonding.

In yet another embodiment, the invention relates to a method for producing a composite component comprising: processing waste fibrous material through an anaerobic digester under conditions to produce anaerobic digested biomass with the desired characteristics, wet-mat forming and cold-pressing the anaerobic digested biomass, and wet-mat drying under heat and pressure. In yet another embodiment, the anaerobic digested biomass may undergo fiber processing to separate the fiber bundles into individual fibers and to break down large constituents left in the digester.

In still yet another embodiment, a liquid effluent portion of the digester solids can be used with the anaerobic digested biomass. The liquid effluent provides an additional source of protein that aids in the fiber-to-fiber bonding.

In yet another embodiment, the invention relates to a method for producing a composite component comprising: digesting waste fibrous material through an anaerobic digester to produce digested biomass and liquid effluent; wet-mat forming and cold-pressing a composition comprising digested biomass and liquid effluent; and drying the formed wet-mat under heat and pressure to produce a composite component. In another embodiment, the digested biomass comprises about 50% less carbohydrate content than the initial waste fibrous material. In still yet another embodiment, the digested biomass comprises about 20% more lignin content than the initial waste fibrous material. In another embodiment, the liquid effluent comprises about 25% more protein after anaerobic digestion of the waste fibrous material as compared to the material prior to digestion.

In yet another embodiment, wet-mat forming uses mechanical pressure to remove free liquid from the mat. In still another embodiment, the moisture content of the mat is about 50-65% after wet-mat forming. In yet another embodiment, drying the formed wet-mat induces fiber-to-fiber binding and fiber-to-effluent-fiber binding, wherein said binding is enhanced by denatured proteins.

In still another embodiment, conditions in the anaerobic digester are controlled, including but not limited to the time period for which the fibers are digested, such that the anaerobic digested biomass has increased in cellulose content and decreased in carbohydrate content. In still another embodiment, after processing through the anaerobic digestor, the anaerobic digested biomass has increased in lignin content. In another embodiment, the methods of the invention produce composite components that are less susceptible to warping and show higher resistance to mold, fungal and bacterial attack.

In yet another embodiment, the method uses properties of both the digested fibers and liquid effluent to control the forming conditions and optimize the performance of the composite component.

In another embodiment, the wet-mat forming and cold-pressing produces wet-mats with significantly lower moisture contents than traditional processes that use recycled or other paper-like pulp fiber. Wet-press pressure is used to consolidate the wet-mat and to remove mechanically as much water as possible before heat-drying.

In yet another embodiment, the drying process is performed under high-pressure and high-temperature that promotes optimum performance characteristics. The wet-formed mat drying process uses natural fiber-to-fiber and fiber-to-effluent bonding to process a composite component with the desired characteristics of strength and durability.

In another embodiment, the drying process is performed under conditions that denature proteins. The denatured proteins enhance fiber-to-fiber binding and fiber-to-effluent-to-fiber binding. The proteins are present in the digested biomass and liquid effluent, and therefore, no extraneous chemicals, resins, waxes or additives need to be added.

In still another embodiment, the invention relates to a method for producing a composite component comprising: digesting waste fibrous material through an anaerobic digester to produce digested biomass and liquid effluent; wet-mat forming and cold-pressing a composition comprising digested biomass and liquid effluent; and drying the formed wet-mat under heat and pressure sufficient to denature proteins, wherein the denatured proteins aid in fiber-to-fiber binding and fiber-to-effluent-to-fiber binding, thereby producing a composite component. In yet another embodiment, the composition further comprises a cellulosic fiber including but not limited to: recycled paper, paper pulp, and old corrugated containers.

In another embodiment, agents to denature proteins can be added at any stage of the process including but not limited to before, during and after the anaerobic digestion process, before, during and after fiber processing, and before, during or after wet-mat forming.

In still another embodiment, the invention relates to a method for producing a composite component comprising: digesting waste fibrous material through an anaerobic digester to produce a first composition comprising digested biomass and liquid effluent; mixing said first composition with cement to produce a second composition; wet-mat forming and cold-pressing said second composition; and curing the formed wet-mat to produce a composite component. In another embodiment, the mixing step further comprises combining a cellulosic fiber with the first composition during cement addition, wherein the cellulosic fiber is selected from the group consisting of: recycled paper, paper pulp, and old corrugated containers.

DETAILED DESCRIPTION

Definitions

Figure 1:
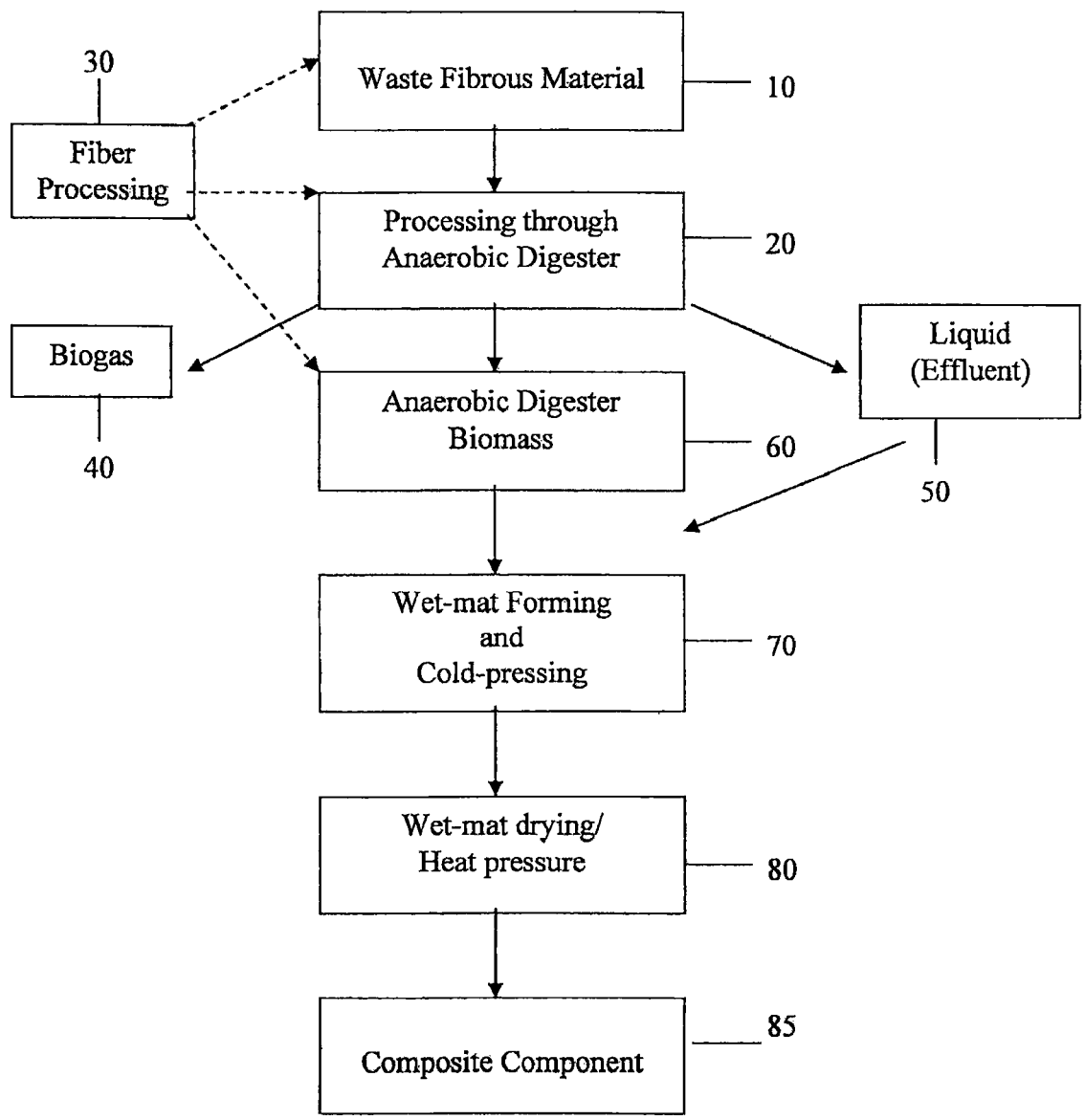
FIG. 1 is a flowchart illustrating a method for producing composite components from waste fibrous material.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values that are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the temperature and pressure used for hot pressing, and the amount of moisture in a composite component.

As used herein, the singular forms "a," "an," and "the" refer to one or more than one, unless the context clearly dictates otherwise.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

As used herein, the term "composite component" or "composite materials" means a fiber-based material. The fibers may be continuous fibers, short fibers, or whiskers.

As used herein, the term "fiber processing" means altering the dimensions and characteristics of fibers and fiber bundles in waste fibrous material, and is meant to include separating individual fibers of a fiber bundle. The fibers and fiber bundles can be altered using mechanical machinery, automated machinery, enzymatic reactions, chemical compositions and solutions, and manual force.

As used herein, the term "manure" is meant to refer herein to animal wastes including animal dejections, feed remains and hair.

The invention relates to methods for producing composite components comprising: processing waste fibrous material through an anaerobic digester; wet-mat forming and cold-pressing the anaerobic digested biomass; and wet-mat drying under heat and pressure. In another embodiment, waste fibrous material may undergo fiber processing either prior to the start of anaerobic digestion, during any time period during anaerobic digestion, or after anaerobic digestion has taken place. In still yet another embodiment, fiber processing may occur at multiple time points during the production of the composite component.

In still yet another embodiment, the invention relates to methods for producing composite components comprising: processing waste fibrous material through an anaerobic digester; wet-mat forming and cold-pressing the anaerobic digested biomass and effluent from the digester; and wet-mat drying under heat and pressure. In another embodiment, the anaerobic digested biomass can be mixed with another material including but not limited to recycled paper, paper pulp, and old corrugated containers ("OCC").

In yet another embodiment, the invention relates to methods for producing composite components without the need for resins, waxes, sizing components or earthworms.

In yet another embodiment, the invention relates to co-processing through the digester with non-manure fibers from other cellulosic materials including but not limited to other agricultural residues, wood fibers/bundles, recycled paper fibers, bamboo/bamboo fibers, etc.

In yet another embodiment, the invention relates to methods for producing composite components by combining post treated fibers with synthetic fibers that may include polymer fibers, electrically conductive polymer fibers, bio-polymers, metallic fibers, or inorganic fibers. The composite may be bonded through natural bonding mechanism, natural or synthetic resins or polymer melting.

Methods for Producing a Composite Component

FIG. 1 provides a flowchart of the processes that may be used to produce the composite components. Waste fibrous material (10) is collected and placed into an anaerobic digester (20). Fiber processing (30) is not required but if desired, fiber processing can occur at any stage prior to anaerobic digestion, at any time period during anaerobic digestion, and after anaerobic digestion. Processing through the anaerobic digester produces gas (40), liquid (50), and anaerobic digested biomass (60). The anaerobic digested biomass (60) can be used alone for further processing or can be used with liquid (50) from the digestor. The anaerobic digested biomass (60) is then used for wet-mat forming and cold-pressing (70) and wet-mat drying/heat pressure (80). A composite component (85) with desired characteristics is produced. Each step of the process is described in further detail below.

Collection of Waste Fibrous Material

Waste fibrous material may be collected using any suitable means in the art. Waste fibrous material includes but is not limited to wood, grass, agricultural residue, manure, recycled waste paper, and agricultural waste materials. Examples of sources of waste fibrous materials include, but are not limited to, livestock production facilities, such as cattle, swine, goat, sheep, diary cow, horse and the like, chicken ranches, turkey farms, duck farms, geese farms, human waste, and the like. Waste fibrous material may also include many forms of agricultural products processing facilities that may include non-food related agricultural products. Waste fibrous material may also include some forms of commingled wastes where a portion of the waste may also include food scraps. Waste fibrous material also may include commingled fibers with spoiled foods.

In another embodiment, the waste fibrous material also may include hay, straw, and other material commonly used in animal stalls or other agriculture environment. In yet another embodiment, the waste fibrous material also may contain urine plus water used in cleaning the stalls. In still yet another embodiment, the waste fibrous material may also contain additional material, such as twine, rope, and other material that may or may not be biodegradable. In yet another embodiment, the waste fibrous material is from a diary farm.

In another embodiment, the waste fibrous material also may include fibers from non-food agricultural products such as bamboo, oil palm, coir, etc.

Processing Through an Anaerobic Digester

The anaerobic digester can be viewed as a chemical reactor that modifies the waste fibrous material as it passes through the digester. In one embodiment, the anaerobic digester is controlled to manipulate the characteristics of the final anaerobic digested biomass and resulting products.

In another embodiment, the conditions and parameters of anaerobic digestion are designed such that the anaerobic digested biomass is decreased in carbohydrate content (hemicelluloses) and increased in cellulose as a percent of dry solid material. The processing parameters also can be controlled so that the lignin content increases with time in the anaerobic digester. Controlling the processing parameters within the anaerobic digester will have an impact on how the waste fibrous material is processed and how the anaerobic digester biomass and resulting products will perform in various applications.

For example, carbohydrates are amorphous and contain water and are highly influenced by water. By reducing the carbohydrate percent in a fiber, the fiber will be more hydrophobic or less affected by water and changing moisture content. For fiber-based composites, dimensional stability is tied to the moisture characteristics of the fiber. The more a fiber absorbs moisture from the environment, the more the panel changes dimensions. A fiber-based composite that is significantly affected by large differentials of moisture absorption could be affected by warping, which could significantly impact the performance of the composite.

With fewer carbohydrates, it is possible to reduce warping of the final composite product. Products with less residual moisture also reduce the potential for fungal, mold and bacterial attack. The reactions within the anaerobic digester can be manipulated to optimize for carbohydrate reduction. The anaerobic digested biomass would have fewer carbohydrates, which is a characteristic that can be used to influence performance properties of the resulting composite component.

Several types of anaerobic digesters exist including simple unheated systems such as covered lagoons and more complex systems that are heated to about 100° F. or higher. Maintaining higher constant temperature reduces reactor volumes required to treat and stabilize waste. A conventional anaerobic digester system generally includes the following components: manure transfer and mixing pit, a digester made of steel, fiberglass, concrete, earth or other suitable material (including heating and mixing equipment if needed), biogas handling and transmission, and gas end use (combustion) equipment such as electric generation equipment.

Conventional anaerobic digesters can also require significant operational oversight depending on operational mode and temperature. Conventional anaerobic digester systems also require proper design and sizing to maintain critical bacterial populations responsible for waste treatment and stabilization for sustained long-term predictable performance. Sizing requirements are based on hydraulic retention time (HRT), and loading rate, where the operating temperature affects these sizing parameters. These factors (size, materials, operational requirements) affect digester costs, which may be fairly capital intensive, and in some economies and farm scales, may not be affordable or may be inoperable if experienced technicians are not available.

In one embodiment, anaerobic digesters having any type of process configuration can be used including but not limited to batch, continuous, mesophilic temperature, thermophilic temperature, high solids, low solids, single-stage complexity and multistage complexity.

In another embodiment, a batch system of anaerobic digestion can be used. Biomass is added to the reactor at the start of the process in a batch and is sealed for the duration of the process. Batch reactors suffer from odor issues that can be a severe problem when they are emptied. Typically biogas production will be formed with a normal distribution pattern over time. The operator can use this fact to determine when they believe the process of digestion of the organic matter has completed.

In yet another embodiment, a continuous system of anaerobic digestion can be used. In continuous digestion processes, organic matter is typically added to the reactor in stages. The end products are constantly or periodically removed, resulting in constant production of biogas. Examples of this form of anaerobic digestion include, continuous stirred-tank reactors (CSTRs), Upflow anaerobic sludge blanket (UASB), Expanded granular sludge bed (EGSB) and Internal circulation reactors (IC).

In still another embodiment, mesophilic or thermophilic operational temperature levels for anaerobic digesters can be used. Mesophilic temperature levels take place optimally around 37°-41° C. or at ambient temperatures between 20°-45° C.; under these temperatures, mesophiles are the primary microorganism present. Thermophilic temperature levels take place optimally around 50°-52° C. and at elevated temperatures up to 70° C.; under these temperatures, thermophiles are the primary microorganisms present.

There are a greater number of species of mesophiles than thermophiles. Mesophiles are also more tolerant to changes in environmental conditions than thermophiles. Mesophilic systems are therefore considered to be more stable than thermophilic digestion systems.

In another embodiment, anaerobic digesters can either be designed to operate in a high solid content, with a total suspended solids (TSS) concentration greater than 20%, or a low solids concentration with a TSS concentration less than 15%. High-solids digesters process a thick slurry that requires more energy input to move and process the feedstock. The thickness of the material may also lead to associated problems with abrasion. High-solids digesters will typically have a lower land requirement due to the lower volumes associated with the moisture.

Low-solids digesters can transport material through the system using standard pumps that require significantly lower energy input. Low-solids digesters require a larger amount of land than high-solids due to the increased volumes associated with the increased liquid:feedstock ratio of the digesters. There are benefits associated with operation in a liquid environment as it enables more thorough circulation of materials and contact between the bacteria and food. This enables the bacteria to more readily access the substances they are feeding off and increases the speed of gas yields.

In still another embodiment, digestion systems can be configured with different levels of complexity: one-stage or single-stage and two-stage or multistage. A single-stage digestion system is one in which all of the biological reactions occur within a single sealed reactor or holding tank. Utilizing a single-stage reactor reduces the cost of construction; however there is less control of the reactions occurring within the system. For instance, acidogenic bacteria, through the production of acids, reduce the pH of the tank, while methanogenic bacteria operate in a strictly defined pH range. Therefore, the biological reactions of the different species in a single-stage reactor can be in direct competition with each other. Another one-stage reaction system is an anaerobic lagoon. These lagoons are pond-like earthen basins used for the treatment and long-term storage of manures. In this case, the anaerobic reactions are contained within the natural anaerobic sludge contained in the pool.

In a two-stage or multi-stage digestion system, different digestion vessels are optimized to bring maximum control over the bacterial communities living within the digesters. Acidogenic bacteria produce organic acids and grow and reproduce faster than methanogenic bacteria. Methanogenic bacteria require stable pH and temperature in order to optimize their performance.

The residence time in a digester varies with the amount and type of waste fibrous material, the configuration of the digestion system and whether it is one-stage or two-stage. In the case of single-stage thermophilic digestion residence times may be in the region of 14 days, which comparatively to mesophilic digestion is relatively fast. The plug-flow nature of some of these systems will mean that the full degradation of the material may not have been realized in this timescale. In this event, digestate exiting the system will be darker in color and will typically have more odor.

In two-stage mesophilic digestion, residence time may vary between 15 and 40 days. In the case of mesophilic UASB digestion, hydraulic residence times can be (1 hour-1 day) and solid retention times can be up to 90 days. In this manner, the UASB system is able to separate solid and hydraulic retention times with the utilization of a sludge blanket.

Continuous digesters have mechanical or hydraulic devices, depending on the level of solids in the material, to mix the contents enabling the bacteria and the food to be in contact. They also allow excess material to be continuously extracted to maintain a reasonably constant volume within the digestion tanks.

In one embodiment, the waste fibrous material can be processed through an anaerobic digester available from GHD, Inc. (Chilton, Wis.). In one embodiment, the waste fibrous material can be processed through an anaerobic digester as described in any of U.S. Pat. Nos. 4,994,237; 6,451,589; 6,613,562; 7,078,229; and 7,179,642; each of which are incorporated by reference in their entirety. Each of the patents recited above is assigned to GHD, Inc., and names Mr. Steve Dvorak as the sole inventor. In yet another embodiment, the anaerobic digester can be a two-stage mixed plug flow digester system In another aspect, the invention may provide a method for the anaerobic digestion of high-solids waste comprising moving the solid waste in a corkscrew-like fashion through the digester. The digester is a generally U-shaped tank with overall horizontal dimensions of approximately 100 feet long and 72 feet wide. A center wall approximately 90 feet in length divides the digester into the two legs of the U-shape. Thus each leg of the digester is approximately 100 feet long and 36 feet wide.

Modified plug flow or slurry flow can be used to move the sludge. The digester heating pipes locally heat the sludge using hot water at approximately 160° F. from the cooler of the engine, causing the heated mixed sludge to rise under convective forces. The convection develops a current in the digester that is uncharacteristic of other high-solids digesters. Sludge is heated by the digester heating pipes near the digester center wall, such that convective forces cause the heated sludge to rise near the center wall. At the same time, sludge near the relatively cooler outer wall falls under convective forces. As a result, the convective forces cause the sludge to follow a circular flow path upward along the center wall and downward along the outer wall. At the same time, the sludge flows along the first and second legs of the digester, resulting in a combined corkscrew-like flow path for the sludge.

In another embodiment (not shown), hot gas injection jets using heated gases from the output of the engine replace the hot water digester heating pipes as a heating and current-generating source. The injection of hot gases circulates the sludge through both natural and forced convection. A similar corkscrew-like flow path is developed in the digester.

To further increase upward flow of the heated sludge near the center wall, biogas may be removed from the biogas storage area in the digester, pressurized with a gas centrifugal or rotary-lobe blower, and injected into the heated sludge through nozzles positioned onto conduit. This recycled biogas injection near the floor of the digester serves to increase the rapidity of the cork-screw-like flow path for the heated sludge.

The U-shape of the digester results in a long sludge flow path and thus a long residence time of approximately twenty days. As the sludge flows through the digester, anaerobic digestion processes the sludge into activated sludge. The anaerobic digestion process also reduces the phosphate content of the liquid effluent after solids removal, by approximately fifty percent, which is a key factor in meeting future environmental regulations.

From the digester, the activated sludge flows into the optional clarifier. The clarifier uses gravity to separate the activated sludge into liquid and solid portions. Under the influence of gravity and separation panels, the liquid portion rises to the top of the mixture and is decanted through a gap into a liquid sump. It is later transferred to lagoon storage through effluent pipe. The liquid is then taken from the lagoon for either treatment or use as fertilizer.

The solid portion of the activated sludge settles to the bottom of the clarifier in the sump. From there, approximately ten to twenty-five percent of the activated sludge is recycled to the digester or mixing chamber through activated sludge recirculation pipe to mix with the incoming manure, as described above. The remaining approximately seventy-five to ninety percent of the activated sludge is removed from the clarifier through sump pipe and is transferred for further processing.

Figure 2:
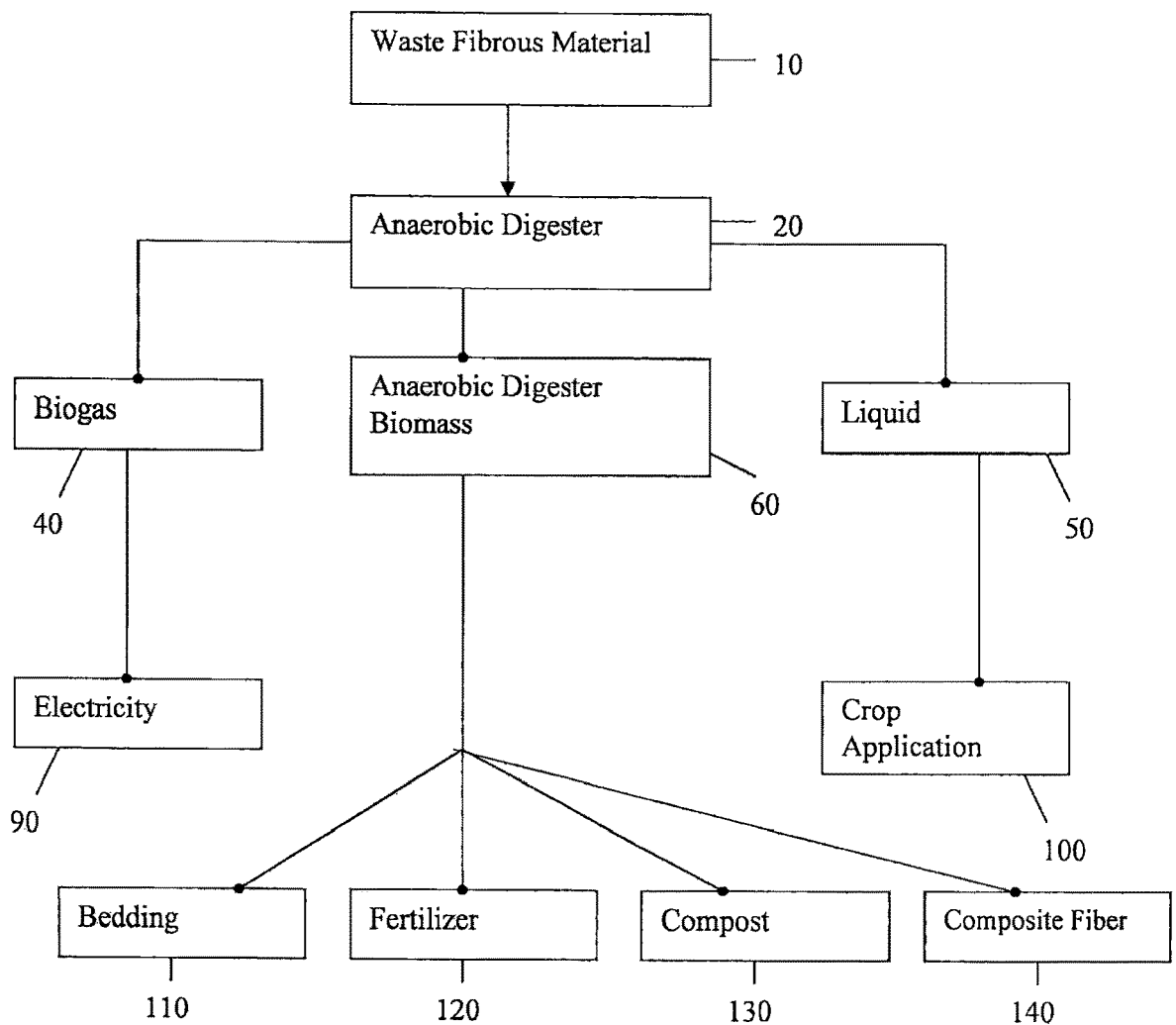
FIG. 2 is a flowchart illustrating the steps involved in an exemplary anaerobic digester.

As shown in FIG. 2, waste fibrous material (10) is collected and placed in the anaerobic digester (20). Waste fibrous material can be processed for any number of days including but not limited to 1-10, 11-20, 21, 22, 23-30, 31-40, and greater than 40. Processing time of the fiber through the digester is dependent on the application or required performance of the composite product. If the digester is to produce fiber for bedding or land application, then the process will be controlled to produce more fiber and a shorter dwell time in the digester will be used. If the digester is run as a chemical reactor to produce fibers for composite products then time will vary based on the input fiber type and the output performance requirements of the composite product. Less time, such as one day, might be used if only surface breakdown of the fiber is desired. Longer times, such as 20 to 40 days, may be used if more complete degradation of the amorphous carbohydrate portion of the fiber needs to be done. Various by-products will be produced from the anaerobic digester including biogas (40), liquid effluent (50) and fibrous residual known as anaerobic digester biomass (60). The biogas may include methane, ammonia, and $CO_2$, and can be used as a source of electricity (90). The liquid effluent (50) can be used for crop application (100). Finally, anaerobic digester biomass (60) is produced, and can be used for animal bedding (110), fertilizer (120) or compost (130). The anaerobic digester biomass can be further processed to produce a composite fiber (140).

Fiber Processing

Waste fibrous material processed through the digester yields a biomass product with fibers with a higher portion of crystalline cellulose and lower proportion of carbohydrates. In addition, there also may be residual seeds and seed hulls that pass through the digester. These articles may have an effect on the mat forming, basic composite component characteristics, and properties of the final composite component.

In yet another embodiment, fiber processing may be used to the separate the fibers into individual fibers. In still another embodiment, mechanical energy can be used separate the fibers and/or to break down the seed hulls and other larger constituents left in the digester. In another embodiment, fiber processing can occur immediately prior to anaerobic digestion or at the start of anaerobic digestion. In still another embodiment, fiber processing can occur when the anaerobic digestion is 10-20, 20-30, 30-40, 40-50, 50-60, 60-70, 70-80, 80-90, or 90-99% complete. In still another embodiment, fiber processing can occur upon completion of the anaerobic digestion process. In yet another embodiment, the step of fiber processing comprises passing the waste fibrous material at any point in anaerobic digestion through an "in vessel" composter.

In another embodiment, a single-rotating plate refiner at atmospheric pressure may be used for fiber processing. The single-rotating plate can be used to break-up the fibers, resulting in increased surface area for eventual fiber-to-fiber processing.

In still another embodiment, a minimal amount of mechanical energy is used to reduce the size of the particles so that they are the size of the fiber, which can improve the performance characteristics of the composite component. In yet another embodiment, fiber processing is used to change the characteristics of the fibers in the solids and to separate fiber bundles, thereby making it easier for subsequent modification to the fiber, including but not limited to passing through a mechanical pulper, to separate the fiber into small bundles or single fibers and fractional components of seeds and hulls.

Anaerobically Digested Biomass

Anaerobic digested biomass is a stable organic material comprised largely of lignin and cellulose, but also of a variety of mineral components in a matrix of dead bacterial cells. Most of the carbohydrates (sugars) have been converted by the bacteria and what remains is a more crystalline fiber fraction. The reduction of the carbohydrates was verified from a chemical analysis of the anaerobically digested material.

Figure 3:
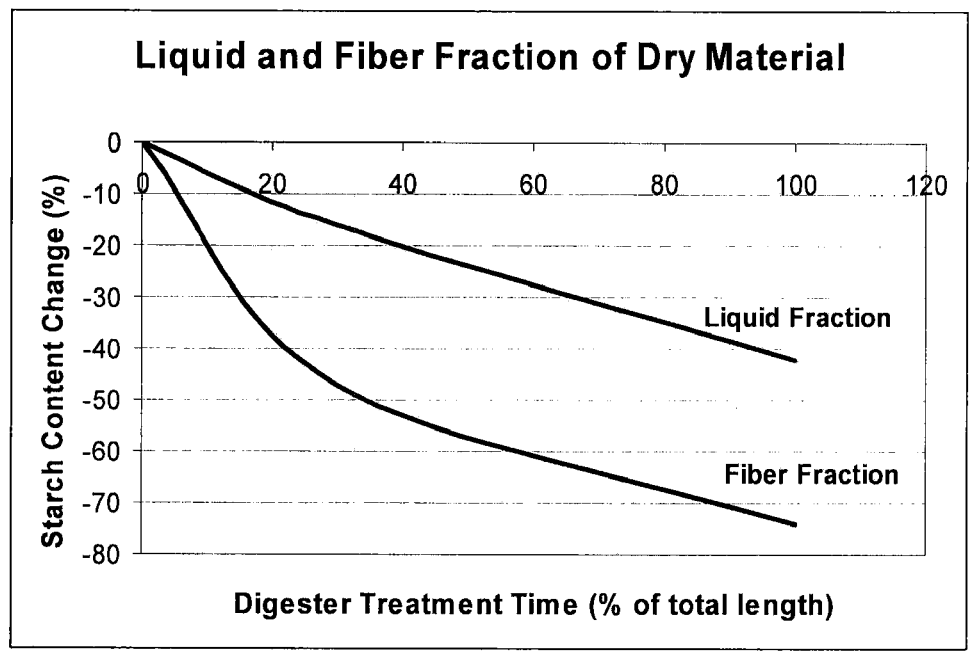
FIG. 3 is a graph showing carbohydrate content as a function of digestion time.

The chemical analysis compared manure as it entered the digester with two other measurements approximately 6 days and 22 days in the digester. The chemical analysis showed that starches (a carbohydrate) and non-fiber carbohydrates decreased with time in the digester. FIG. 3 shows that carbohydrates (starches) decreased for both the liquid and fiber fractions as a percent of the initial starting point when entering the digester. (The liquid fraction contains small pieces of fibers which when analyzed showed carbohydrate decreasing which then was included in with the liquid fraction.).

In another embodiment, the conditions and incubation periods for anaerobic digestion of the waste fibrous material are designed such that the resulting biomass contains 25-35%, 35-45%, 45-55%, 55-65%, 65-75%, 75-85%, 85-95% and 95-99% less carbohydrate than the starting material entering the digester.

In another embodiment, the conditions and incubation periods for anaerobic digestion of the waste fibrous material are designed such that the resulting liquid effluent contains 10-20%, 20-30%, 30-40%, 40-50%, 50-60%, 60-70%, 70-80%, and 80-99% less carbohydrate than the starting material entering the digester.

Figure 4:
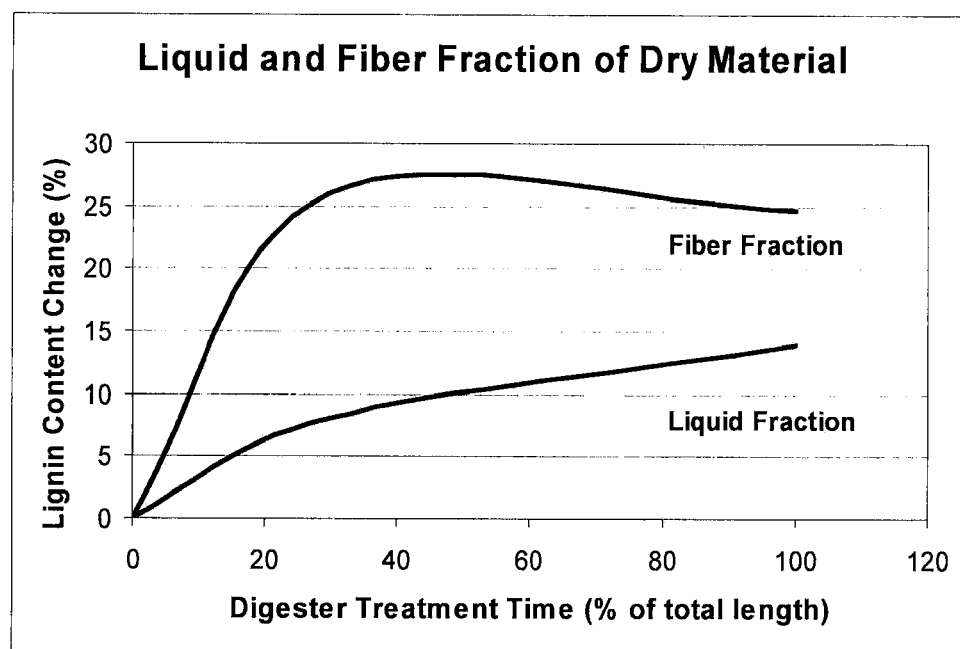
FIG. 4 is a graph showing lignin content as a function of digestion time.

The lignin content increased as a percent of the total dry matter for both the fiber and liquid fractions, as shown in FIG. 4. The increase in lignin content is as expected since as the carbohydrates are consumed in the digester, the total percent of lignin per dry matter should and did increase as the material passed through the digester. Also, as the fibrous material passes through the digester, the fibrous material contains more cellulose, which is the crystalline portion of the cell wall and is naturally hydrophobic (i.e., does not like water). The cellulose content may provide some of the panel's repellency characteristics. Cellulose is also a stronger polymer chain than the amorphous hemicellulose structure. Cellulose has higher stiffness and strength potential, and therefore, methods that increase the cellulose content and the resulting composite components are advantageous.

In another embodiment, the conditions and time periods for anaerobic digestion of the waste fibrous material are designed such that the resulting biomass contains 5-10%, 10-15%, 15-20%, 20-25%, 25-30%, 30-40%, 40-50% and 50-75% increase in the amount of lignin as compared to the starting material entering the digester.

In another embodiment, the conditions and time periods for anaerobic digestion of the waste fibrous material are designed such that the resulting liquid effluent contains 3-5%, 5-10%, 10-15%, 15-20%, 20-25%, 25-30%, 30-40% and 40-75% increase in the amount of lignin as compared to the starting material entering the digester.

Figure 5:
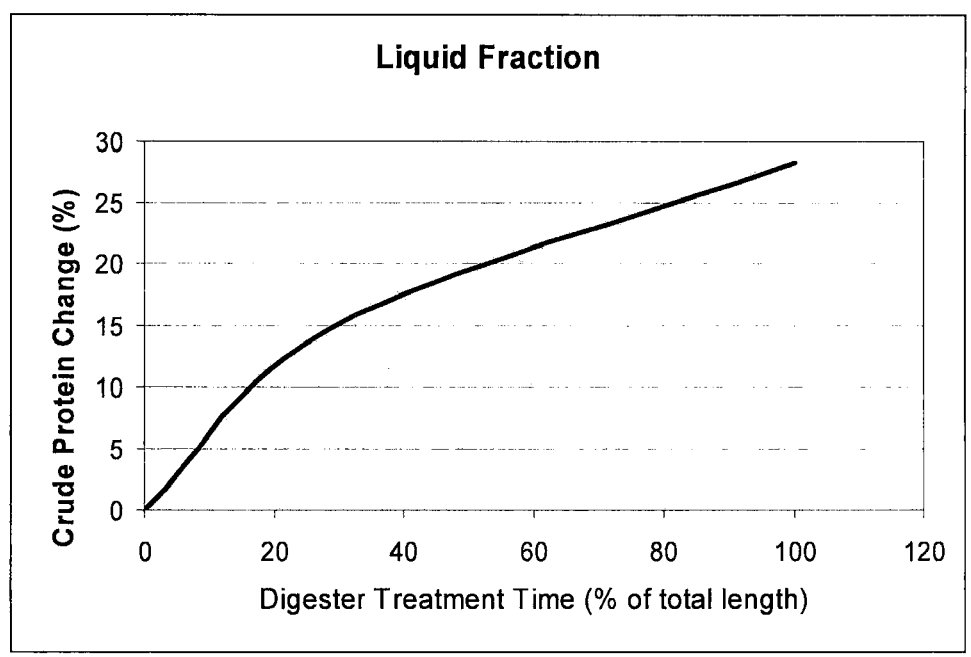
FIG. 5 is a graph showing protein content as a function of digestion time.

Proteins can come from various components in the anaerobic digester process, but they are also a result of dead bacteria. As shown in FIG. 5, analysis of the liquid fraction showed that crude protein increased as the material passes through the digester. Protein is a known natural resin. When heated in the high temperature conditions within the panel, the proteins denature (or denature by chemical means) and provide additional bonding and thereby contribute to the natural water repellency of the resulting composite components.

In yet another embodiment, proteins in the biomass or liquid effluent can be denatured using any suitable means including but not limited to heat, light, ultraviolet light, alcohol, acids, bases, reduced pH, heavy metal salts, heaving metal salts containing $Hg^{+2}$, $Pb^{+2}$, $Ag^{+1}Tl^{+1}$, $Cd^{+2}$, and reducing agents.

In another embodiment, the conditions and time periods for anaerobic digestion of the waste fibrous material are designed such that the resulting liquid effluent contains a 3-5%, 5-10%, 10-15%, 15-20%, 20-25%, 25-30%, 30-40% and 40-75% increase in the amount of protein as compared to the starting material entering the digester.

Wet-Mat Forming and Cold Pressing

In another embodiment, the method of forming composite components comprises forming a wet-mat from the anaerobically digested biomass. The time period of fiber digestion within the anaerobic digester can be used to optimize the performance of the resulting composite components.

In still another embodiment, the anaerobic digested biomass can be used without fiber processing. In the absence of fiber processing, the fiber portion of the anaerobic digested biomass is stiffer, and can provide improved drainage characteristics. The anaerobic digested biomass, in the absence of fiber processing, can also be combined with paper pulps from wood or other cellulosic materials.

In yet another embodiment, the method of forming composite components comprises forming a wet-mat from the anaerobically digested biomass and the liquid effluent from the digestor. The liquid effluent is protein-rich, and can be used to improve composite component properties during the drying process. The anaerobic digested biomass and liquid effluent can be used to impact mat-forming and cold-pressing. The residual proteins within the effluent can serve as a natural resin and help to bond the panel.

In still yet another embodiment, the liquid effluent, which is protein rich, can be used in any amount needed to achieve the desired performance characteristics of the composite components including but not limited to 3-10%, 10-20%, 20-30%, 30-40%, 40-50%, 50-60%, 60-70%, 70-80%, 80-90%, and 90-100% of the liquid effluent relative to the biomass. Optimum amounts are a balance between the effects on processing time and the effects on performance. The protein percent of the effluent can be calculated and used to determine the percent of liquid effluent to be added to the biomass.

In another embodiment, composite panels contain a range between 1% to 10% protein based on dry fiber weight.

In yet another embodiment, the anaerobic digested biomass, alone or in the presence of liquid effluent, can be compacted and formed into a mat of any desired shape. Any forming method can be used, including pressing, casting, molding and the like.

In yet another embodiment, any size wet-forming apparatus can be used including but note limited to 24×24 inch, 36×36 inch, 24×36 inch, 24×48 inch, 48×48 inch, 24×96 inch, 48×96 inch, and 96×96 inch. This may also include continuous length processing methods known to those skilled in the art.

In yet another embodiment, the anaerobic digested biomass, either alone or in the presence of liquid effluent can be mixed with another material including but not limited to recycled old corrugated containers ("OCC") and paper pulp, or any other cellulosic or synthetic fiber to produce a composition that is used for wet-mat forming and cold-pressing. OCC is reclaimed wood fiber from recycled corrugated box stock. The OCC, paper pulp, wood or agricultural residues, can comprise 5-15, 15-25, 25-35, 35-45, 45-55, 55-65, 65-75, 75-80, 80-85, 85-90, 90-95, and greater than 95% of the composition. In still yet another embodiment, the OCC can comprise ⅔ of the composition.

In another embodiment, methods for forming a mat comprise using wet-press pressure to consolidate the wet-mat and to remove water mechanically. Wet pressing is used to consolidate the fibers into a coherent structure. Pressure may be applied to a continuous running web of material by a series of nip rolls which, by compressing the sheet, both increase its volumetric density and reduce its water content. Wet-pressing may take place by gradually increasing pressure and increasing water removal, which helps to preserve the product integrity. The equipment is typical hardboard manufacturing practices known to those skilled in the art. Wet mat forming using mechanical pressure removes significantly more free liquid.

Cold-pressing is a consolidating operation in which an assembly is subjected to pressure without the application of heat or drying air until the fiber-to-fiber interface has reached a minimum possible by pressing the free-liquid from between the fibers and the fiber mat has reached an intermediate structural shape.

In still yet another embodiment, mechanical pressure is used to remove liquid such that the moisture content of the resulting product includes but is not limited to 30-35, 35-40, 40-45, 45-50, 50-55, 55-60, 60-65, 65-70, 70-75, but generally less than 75% moisture content. In another embodiment, moisture content is typically between 50 to 65%.

In another embodiment, to prevent the anaerobic digested biomass from settling out of solution, the wet-mat forming process is performed quickly and with agitation to keep the fibers in suspension. Agitation of the materials in solution provides for uniform distribution over the entire forming surface and increases the surface areas of each fiber, which aids in the fiber-to-fiber bonding.

Wet-Mat Drying Under Heat and Pressure

In another embodiment, the method of producing composite components comprises pressing and drying under heat and pressure. After the wet-mat has been formed and wet-pressed, it then can be placed into a hot-press where the panel will be pressed and dried between plates. In still another embodiment, the wet-formed mat drying process is performed under conditions to produce natural fiber-to-fiber and fiber-to-effluent residuals-to-fiber bonding.

In yet another embodiment, wet-mat drying under heat is performed at a sufficient temperature to denature proteins including but not limited to 40-45° C., 45-50° C., 50-55° C., 55-60° C., 60-65° C., 65-70° C., 70-80° C., 80-90° C., 90-100° C., 100-110° C., and greater than 110° C. The denatured proteins may function as a substance to facilitate strong water resistant bonds.

In still another embodiment, wet-mat drying under pressure is performed at a pressure sufficient to place fibers in close proximity to each other including but not limited to 50-100, 100-200, 200-300, 300-400, 400-500, 500-600, 600-700, 700-800, 800-900, 900-1000 and greater than 1000 psi. Pressure will increase fiber-to-fiber interaction and result in improved bonding.

The wet-formed mat drying process uses natural fiber-to-fiber bonding that occurs during the drying process to impart performance characteristics on the resulting composite component. In addition to the fiber-to-fiber bonding, there is also fiber-to-effluent residuals-to-fiber bonding that occurs during this drying process to impart improved performance characteristics.

In yet another embodiment, drying can be done under constant pressure or intermittent pressure. In still another embodiment, drying can be done at any pressure that produces the desired characteristics including but not limited to 50-100, 100-200, 200-300, 300-400, 400-500, 500-600, 600-700, 700-800, 800-900, 900-1000 and greater than 1000 psi. In another embodiment, drying can be done at any temperature that produces the desired characteristics including but not limited to 300-350° F., 350-380° F., 380-400° F., and 400-420° F. Significant thermal degradation of the fibrous materials may occur above 430° F.

Composite Components

The invention further relates to composite components. In one embodiment, the anaerobic digester biomass and the effluent from the digester are mixed together, and further processed as discussed above, to form a composite product with unique characteristics. Composite components made from 100% digested and refined bovine material comprising anaerobic digested biomass and effluent, which were hot-pressed and without resin, exhibited significantly improved water sizing effect, which was not seen with 100% wood fiber (data not shown). Composite components produced from a 50:50 mixture of digested bovine material and recycled paper exhibited improved water resistance compared to a panel made from 100% recycled paper fiber (data not shown). The combination of the fiber and effluent provides improved performance characteristic.

Anaerobic digestion of waste fibrous material using a digester that employs mixed plug flow design and moves solid waste in a corkscrew-like fashion through the digester produces fibers that are less affected by water, thereby resulting in composite components that are less affected by water. Digesters described in U.S. Pat. Nos. 4,994,237; 6,451,589; 6,613,562; 7,078,229; and 7,179,642 are useful for production of composite components with the desired characteristics.

The outer membrane of bacteria is primarily a protein structure. When the nutrient content of the manure decreases during the anaerobic incubation, the ability to support bacterial growth diminishes and the bacteria begin to die. A result of rapid bacterial growth followed by bacteria dying is an increase in protein rich bacteria "bodies" or "shells" in the residual manure bio-mass. When the wet-mat is press-dried, this residual protein acts like a natural resin. The proteins are denatured when they are heated. When heated in a hot-press and under pressure, the internal mat temperature denatures the proteins such that they can act as a resinous material between fibers. By applying pressure, fibers are brought in close contact, resulting in improved bonding throughout the fibrous mat.

The composite components produced by the methods of the invention can be flat or three dimensional. In yet another embodiment, the composite components can be of any size including but not limited to a circle, a square, a rectangle, a triangle, an octagon, oval, pentagon, hexagon, parallelogram, rhombus, kite, and trapezium. The composite components can be of any size including but not limited to 12×12, 12×24, 12×36, 12×48, 12×60, 12×96, 24×24, 24×36, 24×48, 24×60, 24×96, 36×36, 36×48, 36×60, 36×96, 48×48, 48×60, 48×96, 60×60, 60×96, 96×96 inch, including the widths mentioned and continuous lengths.

In another embodiment, the invention relates to a composite component containing fibrous material having an average fiber length of 1 to 3 mm.

In yet another embodiment, the anaerobic digested biomass can be used to produce a semi-wet formed product comprising random layered board made from expressed digester solids without the addition of water or liquid effluent. This product would be made primarily from the fiber fraction. In one embodiment, fiber-to-fiber bonding may result from natural bonding. In yet another embodiment, fiber-to-surface residual effluent-to-fiber bonding may also occur. In yet another embodiment, fiber-to-fiber bonding may result from the addition of additives including chemical, natural and synthetic additives.

In still another embodiment, the anaerobic digested biomass can be used to produce a semi-wet formed product that is an aligned 3 layer board. Generally, fibers used for bovine feed are corn and grass stalks. A portion of the fibers that pass through the cow and the digester maintain straight fiber bundles and are typically 5 to 25 mm in length. These fibers can be easily aligned in a preferred length-direction. Aligned fibers will increase the stiffness of the composite component in that direction. To improve the cross-direction or width direction properties, a middle layer of fibers can be oriented predominantly 90 degrees to the composite component or the fibers can be randomly oriented. The composite component would then have significant stiffness in the length direction with cross direction strength due to the middle ply.

In another embodiment, the anaerobic digester can be used as a bio-processor for other cellulosic fibers that are used as raw material for other processes. The available carbohydrates are digested leaving more of the hydrophobic crystalline cellulose for composite products. The digester would be operated to produce specific quality of fiber while still producing methane for heat or electricity.

In still another embodiment, the anaerobic digested biomass can be used to produce fiber/cement aligned bonded composites and fiber/cement not aligned bonded composites. The digester has removed a significant portion of the carbohydrates "sugars" from the fibers. The curing process of cement is known to be retarded by the presence of sugars, therefore, the anaerobic digested biomass may be excellent filler for some cement boards in the building trades.

Cement powder could be mixed with the semi-dry digester solids or washed fibers and loosely packed for a low density product. Alternatively, the semi-dry fiber could be aligned after the cement has been added and then pressed to a high density to produce aligned-fiber cement composite that could be used as is or formed into a 3D shape for roof or wall panels. The high density product could also be made to form the top and bottom layers of a sandwich panel. The high density faces provide improved bending performance while a low density core provides support for the faces and shear strength. A by-product of the digestion process is $CO_2$, which has been shown to accelerate the curing of cement. It may be possible to separate individual gases from the digester gas, and use the $CO_2$ to accelerate the cure of the cement, thereby making a faster production cycle.

In still another embodiment, the invention relates to a composition comprising the following relation of components in percent: cement 5-85%; liquid effluent 0-20%; and digested biomass 15-95%. In another embodiment, the cement is Portland cement.

In another embodiment, the invention relates to a method for producing a composite component comprising: digesting waste fibrous material through an anaerobic digestor; wet-mat forming and cold-pressing the anaerobic digested biomass and liquid effluent from the digestor; and wet-mat drying under heat and pressure. In another embodiment, fiber processing can occur prior to the start of processing through an anaerobic digestor, at any time period during processing through the anaerobic digestor, or at the completion of processing through the anaerobic digestion. In still another embodiment, processing through the anaerobic digestion produces anaerobic digested biomass that has decreased in carbohydrate (hemicellulose) content, increased in cellulose content, and increased in lignin content as compared to the waste fibrous material prior to the start of digestion.

In still another embodiment, the invention relates to a method for producing a composite component comprising: digesting waste fibrous material through an anaerobic digestor, wherein the digested fibers are more hydrophobic. In yet another embodiment, the method further comprises wet-mat forming and cold-pressing the anaerobic digested biomass, and wet-mat drying under heat and pressure. The composite components produced by the methods of the invention have increased water-repellency, have improved strength, and can be molded in any shape.

In yet another embodiment, the invention relates to a method comprising: wet-mat drying anaerobic digested biomass and liquid effluent from the digester under a temperature that denatures proteins and a pressure that produces fiber-to-fiber bonding and fiber-to-effluent-to-fiber binding.

Although the invention has been described in considerable detail by the preceding specification, this detail is for the purpose of illustration and is not to be construed as a limitation upon the following claims. All U.S. patents, U.S. patent applications, and U.S. patent application Publications are incorporated herein by reference.

What is claimed is:

1. A method for producing a composite component comprising:
    (a) separating anaerobically digested waste material from an anaerobic digester into digested biomass and liquid effluent;
    (b) processing the separated digested biomass of step (a) to break fibers and fiber bundles;
    (c) mixing the separated, processed biomass from step (b) with liquid effluent from the digester to form a composition;
    (d) wet-mat forming and cold-pressing the composition from step (c) and;
    (e) drying the formed wet-mat from step (d) to produce a composite component.

2. The method of claim 1, wherein step (c) further comprises mixing a cellulosic fiber with the composition.

3. A method for producing a composite component comprising:
    (a) mixing digested biomass from an anaerobic digester with liquid effluent from the anaerobic digester to form a digested biomass composition;
    (b) wet-mat forming the digested biomass composition directly from step (a); and
    (c) drying the formed wet-mat from step (b) to produce a composite component.

4. A method for producing a composite component comprising:
    (a) processing digested biomass from an anaerobic digester;
    (b) combining the processed, digested biomass with liquid from said digester to form a composition; and
    (c) wet-mat forming the composition.

5. The method of claim 4, wherein the composition further comprises a cellulosic fiber.

6. The method of claim 2, wherein the cellulosic fiber is selected from the group consisting of: recycled paper, paper pulp, and old corrugated containers.

7. The method of claim 1, wherein wet-mat forming uses mechanical pressure to remove free liquid from the mat.

8. The method of claim 1, wherein the moisture content of the mat is about 50-65%.

9. The method of claim 1, wherein drying is performed at temperatures from 380° to 420° F.

10. The method of claim 1, wherein the drying is performed under constant pressure from 60 to 1000 psi.

11. The method of claim 3, further comprising mixing a cellulosic fiber with the digested biomass composition prior to step (b).

12. The method of claim 3, wherein the cellulosic fiber is selected from the group consisting of: recycled paper, paper pulp, and old corrugated containers.

13. The method of claim 3, wherein the cellulosic fiber is from about 45% to about 55% of the digested biomass composition.

14. The method of claim 3, wherein the cellulosic fiber is about 50% of the digested biomass composition.

15. The method of claim 5, wherein the cellulosic fiber is selected from the group consisting of: recycled paper, paper pulp, and old corrugated containers.

16. The method of claim 5, wherein the cellulosic fiber is about 50% of the digested biomass composition.

17. The method of claim 1, wherein the liquid effluent in step (c) relative to the digested biomass is selected from the group consisting of: 3-10%, 10-20%, 20-30%, 30-40%, and 40-50%.

18. The method of claim 1, wherein the liquid effluent in step (c) relative to the digested biomass is from 3-10%.

19. The method of claim 1, wherein the liquid effluent in step (c) relative to the digested biomass is from 10-20%.

20. The method of claim 4, wherein the liquid relative to the digested biomass is selected from the group consisting of: 3-10%, 10-20%, 20-30%, 30-40%, and 40-50%.

* * * * *